United States Patent
Sandhu

(10) Patent No.: US 10,835,739 B2
(45) Date of Patent: Nov. 17, 2020

(54) ELECTRICAL STIMULATION LEADS AND SYSTEMS WITH ELONGATE ANCHORING ELEMENTS AND METHODS OF MAKING AND USING

(71) Applicant: Boston Scientific Neuromodulation Corporation, Valencia, CA (US)

(72) Inventor: Neil Singh Sandhu, Boulder, CO (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 451 days.

(21) Appl. No.: 15/920,203

(22) Filed: Mar. 13, 2018

(65) Prior Publication Data

US 2018/0272125 A1 Sep. 27, 2018

Related U.S. Application Data

(60) Provisional application No. 62/476,232, filed on Mar. 24, 2017.

(51) Int. Cl.
*A61N 1/05* (2006.01)

(52) U.S. Cl.
CPC .... *A61N 1/0558* (2013.01); *A61N 2001/0582* (2013.01)

(58) Field of Classification Search
CPC ...... A61N 1/0558; A61N 1/057; A61N 1/059; A61N 1/37518; A61N 2001/0582
See application file for complete search history.

(56) References Cited

U.S. PATENT DOCUMENTS

| | | | |
|---|---|---|---|
| 376,810 | A | 1/1888 | Brill |
| 612,685 | A | 10/1898 | Thorp et al. |
| 2,046,837 | A | 7/1936 | Phillips |
| 3,333,045 | A | 7/1967 | Fisher et al. |
| 3,866,615 | A | 2/1975 | Hewson |
| 3,918,440 | A | 11/1975 | Kraus |
| 4,141,752 | A | 2/1979 | Shipko |

(Continued)

FOREIGN PATENT DOCUMENTS

| | | |
|---|---|---|
| AU | 2012201634 | 4/2012 |
| EP | 85417 A1 | 8/1983 |

(Continued)

*Primary Examiner* — Tammie K Marlen
(74) *Attorney, Agent, or Firm* — Lowe Graham Jones PLLC; Bruce E. Black

(57) ABSTRACT

A stimulation lead anchoring system includes a lead anchor and a removable inner core. The lead anchor includes an anchor body that includes a lead lumen that extends longitudinally along the anchor body and is configured and arranged to receive a portion of an electrical stimulation lead. The removable inner core includes a core body that includes an inner lumen that extends longitudinally along the core body. The lead anchor and removable inner core are configured and arranged to expand the anchor body when a portion of the core body is inserted into the lead lumen to facilitate receiving the portion of the electrical stimulation lead into the lead lumen and inner lumen and slidably positioning the lead anchor along the lead. The anchor body is configured and arranged to engage the portion of the electrical stimulation lead upon withdrawal of the core body from the lead lumen.

20 Claims, 8 Drawing Sheets

(56) References Cited

U.S. PATENT DOCUMENTS

| | | |
|---|---|---|
| 4,276,882 A | 7/1981 | Dickhudt et al. |
| 4,316,471 A | 2/1982 | Shipko et al. |
| 4,462,401 A | 7/1984 | Burgio |
| 4,632,670 A | 12/1986 | Mueller, Jr. |
| 4,764,132 A | 8/1988 | Stutz, Jr. |
| 4,858,623 A | 8/1989 | Bradshaw et al. |
| 5,036,862 A | 8/1991 | Pohndorf |
| 5,107,856 A | 4/1992 | Kristiansen et al. |
| 5,143,090 A | 9/1992 | Dutcher et al. |
| 5,158,097 A | 10/1992 | Christlieb |
| 5,217,028 A | 6/1993 | Dutcher et al. |
| 5,228,248 A | 7/1993 | Haddock |
| 5,269,809 A | 12/1993 | Hayhurst et al. |
| 5,330,477 A | 7/1994 | Cook |
| 5,370,662 A | 12/1994 | Stone et al. |
| 5,376,108 A | 12/1994 | Collins et al. |
| 5,484,445 A | 1/1996 | Knuth |
| 5,584,874 A | 12/1996 | Rugland et al. |
| 5,628,780 A | 5/1997 | Helland et al. |
| 5,738,521 A | 4/1998 | Dugot |
| 5,746,722 A | 5/1998 | Pohondorf et al. |
| 5,865,843 A | 2/1999 | Baudino |
| 5,876,431 A | 3/1999 | Spehr et al. |
| 5,895,360 A | 4/1999 | Christopherson et al. |
| 5,957,968 A | 9/1999 | Belden et al. |
| 6,104,957 A | 8/2000 | Alo et al. |
| 6,175,710 B1 | 1/2001 | Kamaji et al. |
| 6,181,969 B1 | 1/2001 | Gord |
| 6,192,279 B1 | 2/2001 | Barreras, Sr. et al. |
| 6,224,450 B1 | 5/2001 | Norton |
| 6,271,094 B1 | 8/2001 | Boyd et al. |
| 6,295,944 B1 | 10/2001 | Lovett |
| 6,360,750 B1 | 3/2002 | Gerber et al. |
| 6,364,278 B1 | 4/2002 | Lin et al. |
| 6,391,985 B1 | 5/2002 | Goode et al. |
| 6,473,654 B1 | 10/2002 | Chinn |
| 6,506,190 B1 | 1/2003 | Walshe |
| 6,516,227 B1 | 2/2003 | Meadows et al. |
| 6,606,523 B1 | 8/2003 | Jenkins |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,901,287 B2 | 5/2005 | Davis et al. |
| 6,902,547 B2 | 6/2005 | Aves et al. |
| 6,978,180 B2 | 12/2005 | Tadlock |
| 6,984,145 B1 | 1/2006 | Lim |
| 7,056,333 B2 | 6/2006 | Walshe |
| 7,069,083 B2 | 6/2006 | Finch et al. |
| 7,072,719 B2 | 7/2006 | Vinup et al. |
| 7,161,461 B1 | 1/2007 | Nelson |
| 7,184,841 B1 | 2/2007 | Bodner et al. |
| 7,203,548 B2 | 4/2007 | Whitehurst et al. |
| 7,235,078 B2 | 7/2007 | West, Jr. |
| 7,244,150 B1 | 7/2007 | Brase et al. |
| 7,337,005 B2 | 2/2008 | Kim et al. |
| 7,337,006 B2 | 2/2008 | Kim et al. |
| 7,343,202 B2 | 3/2008 | Mrva et al. |
| 7,402,076 B1 | 7/2008 | Lim |
| 7,437,193 B2 | 10/2008 | Parramon et al. |
| 7,447,546 B2 | 11/2008 | Kim et al. |
| 7,450,993 B2 | 11/2008 | Kim et al. |
| 7,450,997 B1 | 11/2008 | Pianca et al. |
| 7,502,651 B2 | 3/2009 | Kim et al. |
| 7,580,753 B2 | 8/2009 | Kim et al. |
| 7,596,414 B2 | 9/2009 | Whitehurst et al. |
| 7,610,102 B2 | 10/2009 | Kowalczyk |
| 7,610,103 B2 | 10/2009 | Whitehurst et al. |
| 7,672,734 B2 | 3/2010 | Anderson et al. |
| 7,761,165 B1 | 7/2010 | He et al. |
| 7,783,359 B2 | 8/2010 | Meadows |
| 7,787,960 B2 | 8/2010 | Lubenow |
| 7,792,590 B1 | 9/2010 | Pianca et al. |
| 7,809,446 B2 | 10/2010 | Meadows |
| 7,831,313 B2 * | 11/2010 | Lauro ............... H01R 13/5804 607/126 |
| 7,848,803 B1 | 12/2010 | Jaax et al. |
| 7,853,321 B2 | 12/2010 | Jaax et al. |
| 7,860,568 B2 | 12/2010 | Deininger et al. |
| 7,949,395 B2 | 5/2011 | Kuzma |
| 7,974,706 B2 | 7/2011 | Moffitt et al. |
| 7,993,378 B2 | 8/2011 | Foley et al. |
| 8,019,443 B2 | 9/2011 | Schleicher et al. |
| 8,082,039 B2 | 12/2011 | Kim et al. |
| 8,175,710 B2 | 5/2012 | He |
| 8,204,595 B2 | 6/2012 | Pianca et al. |
| 8,224,450 B2 | 7/2012 | Brase |
| 8,224,451 B2 | 7/2012 | Jaax et al. |
| 8,229,565 B2 | 7/2012 | Kim et al. |
| 8,229,573 B2 | 7/2012 | Chen et al. |
| 8,262,624 B2 * | 9/2012 | Sage ............... A61B 17/10 604/174 |
| 8,271,094 B1 | 9/2012 | Moffitt et al. |
| 8,295,944 B2 | 10/2012 | Howard et al. |
| 8,315,704 B2 | 11/2012 | Jaax et al. |
| 8,364,278 B2 | 1/2013 | Pianca et al. |
| 8,391,985 B2 | 3/2013 | McDonald |
| 8,483,237 B2 | 7/2013 | Zimmermann et al. |
| 8,568,462 B2 | 10/2013 | Sixto et al. |
| 8,647,346 B2 | 2/2014 | Bleich et al. |
| 8,688,232 B2 | 4/2014 | Finley et al. |
| 8,688,235 B1 | 4/2014 | Pianca et al. |
| 8,712,546 B2 | 4/2014 | Kim et al. |
| 8,718,790 B2 | 5/2014 | Pianca |
| 8,768,488 B2 | 7/2014 | Barker |
| 8,774,926 B2 | 7/2014 | Alataris et al. |
| 8,781,603 B2 | 7/2014 | Ye et al. |
| 8,831,742 B2 | 9/2014 | Pianca et al. |
| 8,849,422 B2 | 9/2014 | Pianca |
| 8,897,893 B2 | 11/2014 | Pianca |
| 8,983,624 B2 | 3/2015 | Imran |
| 9,089,694 B2 | 7/2015 | Pianca |
| 9,138,574 B2 | 9/2015 | Kern et al. |
| 9,199,074 B2 | 12/2015 | Pianca |
| 9,205,259 B2 | 12/2015 | Kim et al. |
| 9,205,260 B2 | 12/2015 | Kim et al. |
| 9,259,569 B2 | 2/2016 | Brounstein et al. |
| 2001/0000187 A1 | 4/2001 | Peckham et al. |
| 2002/0107554 A1 | 8/2002 | Biggs et al. |
| 2003/0074023 A1 | 4/2003 | Kaplan et al. |
| 2003/0078623 A1 | 4/2003 | Weinberg et al. |
| 2003/0208247 A1 | 11/2003 | Spinelli et al. |
| 2004/0059392 A1 | 3/2004 | Parramon et al. |
| 2005/0033374 A1 | 2/2005 | Gerber |
| 2005/0033393 A1 | 2/2005 | Daglow |
| 2005/0165465 A1 | 7/2005 | Pianca et al. |
| 2005/0240238 A1 | 10/2005 | Mamo et al. |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0173520 A1 | 8/2006 | Olson |
| 2006/0205995 A1 | 9/2006 | Browning |
| 2006/0206162 A1 | 9/2006 | Wahlstrand et al. |
| 2007/0010794 A1 | 1/2007 | Dann et al. |
| 2007/0050005 A1 | 3/2007 | Lauro |
| 2007/0078399 A1 | 4/2007 | Olson |
| 2007/0100348 A1 | 5/2007 | Cauthen et al. |
| 2007/0112385 A1 | 5/2007 | Conlon |
| 2007/0150036 A1 | 6/2007 | Anderson |
| 2007/0219595 A1 | 9/2007 | He |
| 2007/0239248 A1 | 10/2007 | Hastings et al. |
| 2007/0255369 A1 | 11/2007 | Bonde et al. |
| 2007/0265682 A1 | 11/2007 | Wiegnann et al. |
| 2008/0071320 A1 | 3/2008 | Brase |
| 2008/0091255 A1 | 4/2008 | Caparso et al. |
| 2008/0140130 A1 | 6/2008 | Chan et al. |
| 2008/0140152 A1 | 6/2008 | Imran et al. |
| 2008/0140153 A1 | 6/2008 | Burdulis |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |

(56) References Cited

U.S. PATENT DOCUMENTS

| | | |
|---|---|---|
| 2008/0196939 A1 | 8/2008 | Lubenow et al. |
| 2008/0228251 A1 | 9/2008 | Hill |
| 2008/0243220 A1 | 10/2008 | Barker |
| 2008/0262588 A1 | 10/2008 | Zarembo et al. |
| 2008/0275401 A1 | 11/2008 | Sage et al. |
| 2008/0312712 A1 | 12/2008 | Penner |
| 2009/0018601 A1 | 1/2009 | Deininger et al. |
| 2009/0112272 A1 | 4/2009 | Schleicher et al. |
| 2009/0187222 A1 | 7/2009 | Barker |
| 2009/0198312 A1 | 8/2009 | Barker |
| 2009/0204193 A1 | 8/2009 | Kokones et al. |
| 2009/0210043 A1 | 8/2009 | Reddy |
| 2009/0248095 A1 | 10/2009 | Schleicher et al. |
| 2009/0254151 A1 | 10/2009 | Anderson et al. |
| 2009/0259260 A1 | 10/2009 | Bentley et al. |
| 2009/0270940 A1 | 10/2009 | Deininger |
| 2009/0276021 A1 | 11/2009 | Meadows et al. |
| 2009/0276025 A1 | 11/2009 | Burnes et al. |
| 2009/0281571 A1 | 11/2009 | Weaver et al. |
| 2009/0281576 A1 | 11/2009 | Weaver et al. |
| 2009/0281579 A1 | 11/2009 | Weaver et al. |
| 2010/0076535 A1 | 3/2010 | Pianca et al. |
| 2010/0094425 A1 | 4/2010 | Bentley et al. |
| 2010/0137938 A1 | 6/2010 | Kishawi et al. |
| 2010/0174240 A1 | 7/2010 | Wells et al. |
| 2010/0179562 A1 | 7/2010 | Linker et al. |
| 2010/0241179 A1 | 9/2010 | Gielen et al. |
| 2010/0249875 A1 | 9/2010 | Kishawi et al. |
| 2010/0268298 A1 | 10/2010 | Moffitt et al. |
| 2010/0274336 A1 | 10/2010 | Nguyen-Stella et al. |
| 2010/0286670 A1 | 11/2010 | Doyle et al. |
| 2010/0312319 A1 | 12/2010 | Barker |
| 2011/0004267 A1 | 1/2011 | Meadows |
| 2011/0005069 A1 | 1/2011 | Pianca |
| 2011/0022066 A1 | 1/2011 | Sevrain |
| 2011/0022142 A1 | 1/2011 | Barker et al. |
| 2011/0060395 A1 | 3/2011 | Cantlon |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0178573 A1 | 7/2011 | Nguyen-Stella et al. |
| 2011/0213445 A1 | 9/2011 | Blischak |
| 2011/0238129 A1 | 9/2011 | Moffitt et al. |
| 2011/0264180 A1 | 10/2011 | Hamilton |
| 2011/0276056 A1 | 11/2011 | Grigsby et al. |
| 2011/0313427 A1 | 12/2011 | Gindele et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0101326 A1 | 4/2012 | Simon et al. |
| 2012/0150202 A1 | 6/2012 | Chen et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232626 A1 | 9/2012 | Daglow |
| 2012/0277670 A1 | 11/2012 | Goetz |
| 2012/0283835 A1 | 11/2012 | Bentley et al. |
| 2012/0316615 A1 | 12/2012 | Digiore et al. |
| 2012/0316627 A1 | 12/2012 | Finlay et al. |
| 2012/0323253 A1 | 12/2012 | Garai et al. |
| 2012/0330355 A1 | 12/2012 | Finley et al. |
| 2013/0096659 A1 | 4/2013 | Ranu |
| 2013/0105071 A1 | 5/2013 | Digiore et al. |
| 2013/0149031 A1 | 6/2013 | Changsrivong |
| 2013/0197424 A1 | 8/2013 | Bedenbaugh |
| 2013/0197602 A1 | 8/2013 | Pianca et al. |
| 2013/0204336 A1 | 8/2013 | Sharma |
| 2013/0238023 A1 | 9/2013 | Wales et al. |
| 2013/0261684 A1 | 10/2013 | Howard |
| 2013/0317518 A1 | 11/2013 | Govea |
| 2013/0317583 A1 | 11/2013 | Pianca |
| 2013/0317586 A1 | 11/2013 | Pianca |
| 2013/0317587 A1 | 11/2013 | Barker |
| 2013/0317588 A1 | 11/2013 | Howard et al. |
| 2013/0325091 A1 | 12/2013 | Pianca et al. |
| 2014/0018885 A1 | 1/2014 | Pianca |
| 2014/0039587 A1 | 2/2014 | Romero |
| 2014/0074093 A9 | 3/2014 | Nelson et al. |
| 2014/0180345 A1 | 6/2014 | Chan et al. |
| 2014/0257240 A1 | 9/2014 | Burdulis |
| 2014/0276925 A1 | 9/2014 | Alves et al. |
| 2014/0296953 A1 | 10/2014 | Pianca et al. |
| 2014/0343645 A1 | 11/2014 | Wechter |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0005856 A1 | 1/2015 | Pianca et al. |
| 2015/0018915 A1 | 1/2015 | Leven |
| 2015/0021817 A1 | 1/2015 | Romero et al. |
| 2015/0045864 A1 | 2/2015 | Howard |
| 2015/0045865 A1 | 2/2015 | Nageri et al. |
| 2015/0051674 A1 | 2/2015 | Barner et al. |
| 2015/0051675 A1 | 2/2015 | Barner |
| 2015/0066120 A1 | 3/2015 | Govea |
| 2015/0066121 A1 | 3/2015 | Govea et al. |
| 2015/0099936 A1 | 4/2015 | Burdulis et al. |
| 2015/0134038 A1 | 5/2015 | Spinelli et al. |
| 2015/0151113 A1 | 6/2015 | Govea et al. |
| 2015/0246216 A1 | 9/2015 | Barker |
| 2015/0343198 A1 | 12/2015 | Nageri et al. |
| 2017/0036013 A1 | 2/2017 | Leven |
| 2017/0246454 A1 | 8/2017 | Leven |
| 2017/0333702 A1 | 11/2017 | Barner |
| 2018/0021569 A1 | 1/2018 | Pianca |

FOREIGN PATENT DOCUMENTS

| | | | |
|---|---|---|---|
| EP | 0597213 A1 | 5/1994 |
| WO | 1998033551 A1 | 8/1998 |
| WO | 1999/053994 | 10/1999 |
| WO | 2000/013743 A2 | 3/2000 |
| WO | 2000/064535 | 11/2000 |
| WO | 2003020365 | 3/2003 |
| WO | 2003084398 | 10/2003 |
| WO | 2004/054655 | 7/2004 |
| WO | 2005120203 | 12/2005 |
| WO | 2006029257 | 3/2006 |
| WO | 2006/086363 A2 | 8/2006 |
| WO | 2007041604 | 4/2007 |
| WO | 2007/056384 A2 | 5/2007 |
| WO | 2007/083108 A2 | 7/2007 |
| WO | 2007/149994 A2 | 12/2007 |
| WO | 2008/094789 A1 | 8/2008 |
| WO | 2008101026 A1 | 8/2008 |
| WO | 2008/121708 A2 | 10/2008 |
| WO | 2010083308 | 7/2010 |
| WO | 2010/126853 A1 | 11/2010 |
| WO | 2012151356 A1 | 11/2012 |
| WO | 2013112920 A1 | 8/2013 |

\* cited by examiner

ELECTRICAL STIMULATION LEADS AND SYSTEMS WITH ELONGATE ANCHORING ELEMENTS AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/476,232, filed Mar. 24, 2017, which is incorporated herein by reference.

FIELD

The present invention is directed to the area of implantable electrical stimulation systems and methods of making and using the systems, and in particular lead anchors and methods of making and using the lead anchors.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), at least one lead, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a stimulation lead anchoring system that includes a lead anchor. The lead anchor includes an anchor body that includes a distal end portion, a proximal end portion, a longitudinal length, and a lead lumen that extends longitudinally along the anchor body. The stimulation lead anchoring system also includes a removable inner core and is configured and arranged to receive a portion of an electrical stimulation lead. The removable inner core includes a core body that includes a distal end portion, a proximal end portion, a longitudinal length, and an inner lumen that extends longitudinally along the core body. The lead anchor and removable inner core are configured and arranged to expand the anchor body into an expanded configuration when a portion of the core body is inserted into the lead lumen of the anchor body to facilitate receiving the portion of the electrical stimulation lead into the lead lumen of the lead anchor and the inner lumen of the removable inner core and slidably positioning the lead anchor at a selected position along the lead. The anchor body is configured and arranged to engage the portion of the electrical stimulation lead in the lead lumen upon withdrawal of the core body of the removable inner core from the lead lumen of the anchor body.

In at least some embodiments, the longitudinal length of the core body is at least as long as the longitudinal length of the anchor body. In at least some embodiments, the core body further comprises a slit that extends along the longitudinal length of the core body. In at least some embodiments, the anchor body is configured and arranged to compress the portion of the electrical stimulation lead in the lead lumen upon withdrawal of the core body of the removable inner core from the lead lumen of the anchor body.

In at least some embodiments, the lead anchor further includes at least one suture tab that radially extends from the anchor body. In at least some embodiments, the lead anchor further includes at least two ridges that radially extend from the anchor body and that define at least one suture region between the at least two ridges. In at least some embodiments, the lead anchor further includes at least one suture trough or groove in the anchor body.

In at least some embodiments, the lead anchor further includes a flange that radially extends from either the proximal end portion or distal end portion of the anchor body. In at least some embodiments, the removable inner core further includes a flange that radially extends from the proximal end portion of the core body.

In at least some embodiments, the stimulation lead anchoring system further includes a tool. The tool includes a rail component that includes at least one channel. At least one portion of the at least one channel of the rail component has a diameter that is at least as large as an outer diameter of the core body and is smaller than an outer diameter of the flange of the removable inner core. The tool also includes a slide component configured and arranged to slide along the rail component. The slide component includes at least one channel. At least one portion of the at least one channel of the slide component has a diameter that is at least as large as the outer diameter of the core body and is smaller than an outer diameter of at least one portion of the lead anchor.

In at least some embodiments, the stimulation lead anchoring system further includes a tool. The tool includes a rail component that includes at least one channel. At least one portion of the at least one channel of the rail component has a diameter that is at least as large as an outer diameter of the core body and is smaller than an outer diameter of at least one portion of the lead anchor. The tool also includes a slide component configured and arranged to slide along the rail component. The slide component includes at least one channel. At least one portion of the at least one channel of the slide component has a diameter that is at least as large as the outer diameter of the core body and is smaller than an outer diameter of the flange of the removable inner core.

In at least some embodiments, the stimulation lead anchoring system further includes a tool. The tool includes a rail component. The rail component includes at least one channel. At least one portion of the at least one channel of the rail component has a diameter that is at least as large as an outer diameter of the core body and is smaller than an outer diameter of at least one portion of the lead anchor. The tool also includes a slide component configured and arranged to slide along the rail component. The removable inner core is integral to, or non-removably attached to, the slide component.

In at least some embodiments, the stimulation lead anchoring system further includes the electrical stimulation lead.

Another embodiment is a method of anchoring an electrical stimulation lead with any of the stimulation lead anchoring systems described above. The method includes inserting a portion of the electrical stimulation lead in the lead lumen of the anchor body of the lead anchor and the inner lumen of the core body of the removable inner core while a portion of the core body of the removable inner core is disposed within the lead lumen of the anchor body of the lead anchor; withdrawing the core body of the removable inner core from the lead lumen of the anchor body of the lead anchor so that the lead anchor engages the electrical stimulation lead; and removing the removable inner core from the electrical stimulation lead.

In at least some embodiments, the lead anchor further includes a flange that radially extends from the proximal or distal end portion of the anchor body, and withdrawing the core body of the removable inner core from the lead lumen of the anchor body of the lead anchor includes applying a force against the flange of the lead anchor. In at least some embodiments, the removable inner core further includes a flange that radially extends from the proximal end portion of the core body, and withdrawing the core body of the removable inner core from the lead lumen of the anchor body of the lead anchor includes applying a force against the flange of the removable inner core.

In at least some embodiments, the method further includes inserting another portion of the core body into the lead lumen of the anchor body; repositioning the lead anchor and removable inner core on the electrical stimulation lead to another position on the electrical stimulation lead while the other portion of the core body is disposed within the lead lumen of the anchor body; and withdrawing the core body of the removable inner core from the lead lumen of the anchor body of the lead anchor so that the lead anchor engages the electrical stimulation lead at the other position on the electrical stimulation lead.

In at least some embodiments, the method further includes inserting another portion of the core body into the lead lumen of the anchor body; and removing the lead anchor and removable inner core from the electrical stimulation lead while the other portion of the core body is disposed within the lead lumen of the anchor body.

A further embodiment is a method of employing any of the stimulation lead anchoring systems described above. The method includes inserting a portion of the core body into the lead lumen of the anchor body; and removing the lead anchor and removable inner core from, or repositioning the lead anchor and removable inner core on, the electrical stimulation lead while the portion of the core body is disposed within the lead lumen of the anchor body.

In at least some embodiments, the lead anchor further includes a flange that radially extends from the proximal or distal end portion of the anchor body, and inserting the core body into the lead lumen of the anchor body includes applying a force against the flange of the lead anchor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems, and in particular implantable electrical stimulation leads having elongate anchoring elements and methods of making and using the leads.

Suitable implantable electrical stimulation systems include, but are not limited to, a least one lead with at least one electrode disposed along a distal end of the lead and at least one terminal disposed along the at least one proximal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278;

8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Figure 1:
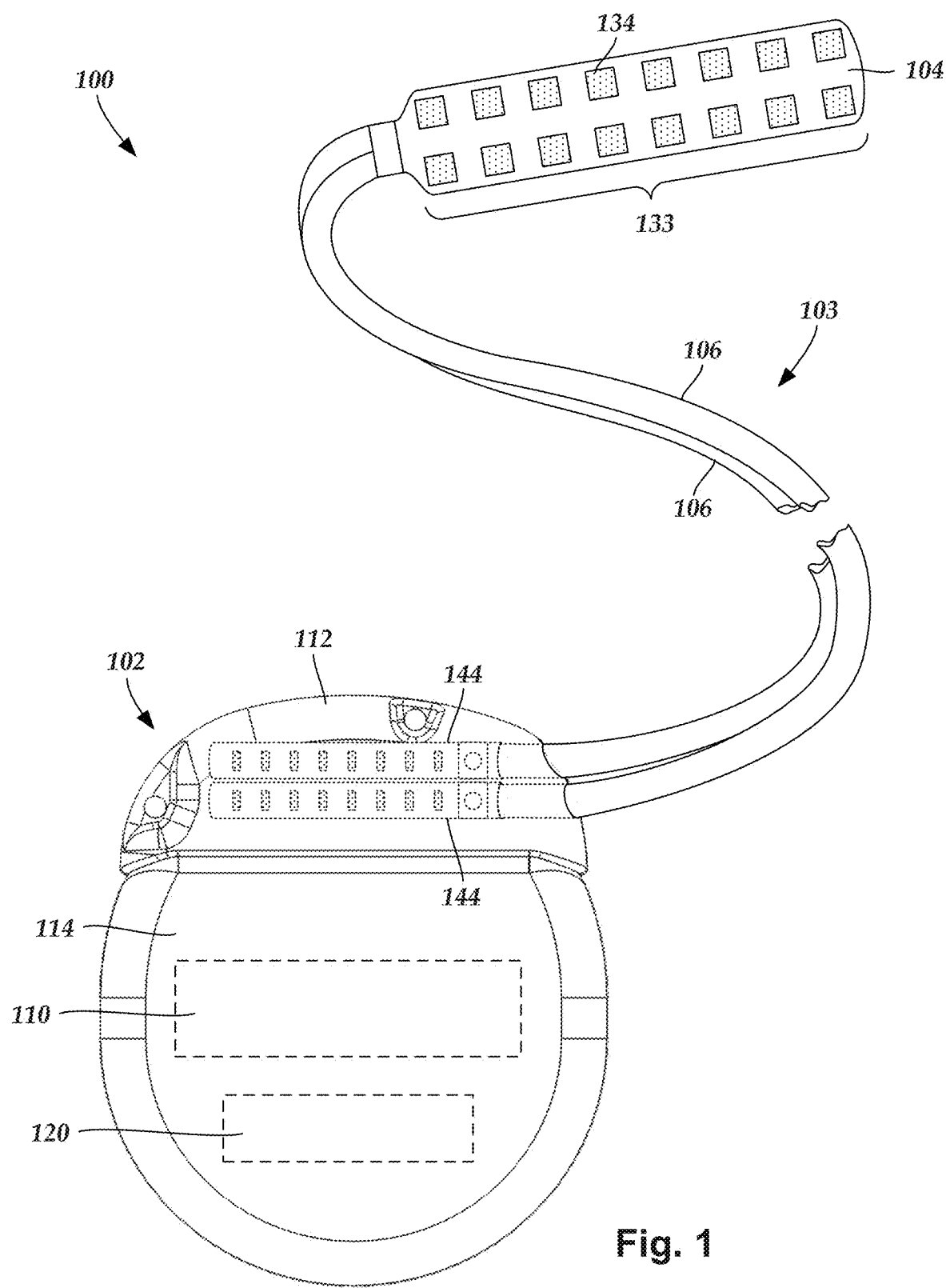
FIG. 1 is a schematic front view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (for example, a stimulator or pulse generator) 102 and a lead 103 coupleable to the control module 102. The lead 103 includes a paddle body 104 and at least one lead body 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (for example, 310 in FIG. 3A) is disposed along each of the at least one lead body 106. In at least some embodiments, there may be a single electrode 134 or a single terminal.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
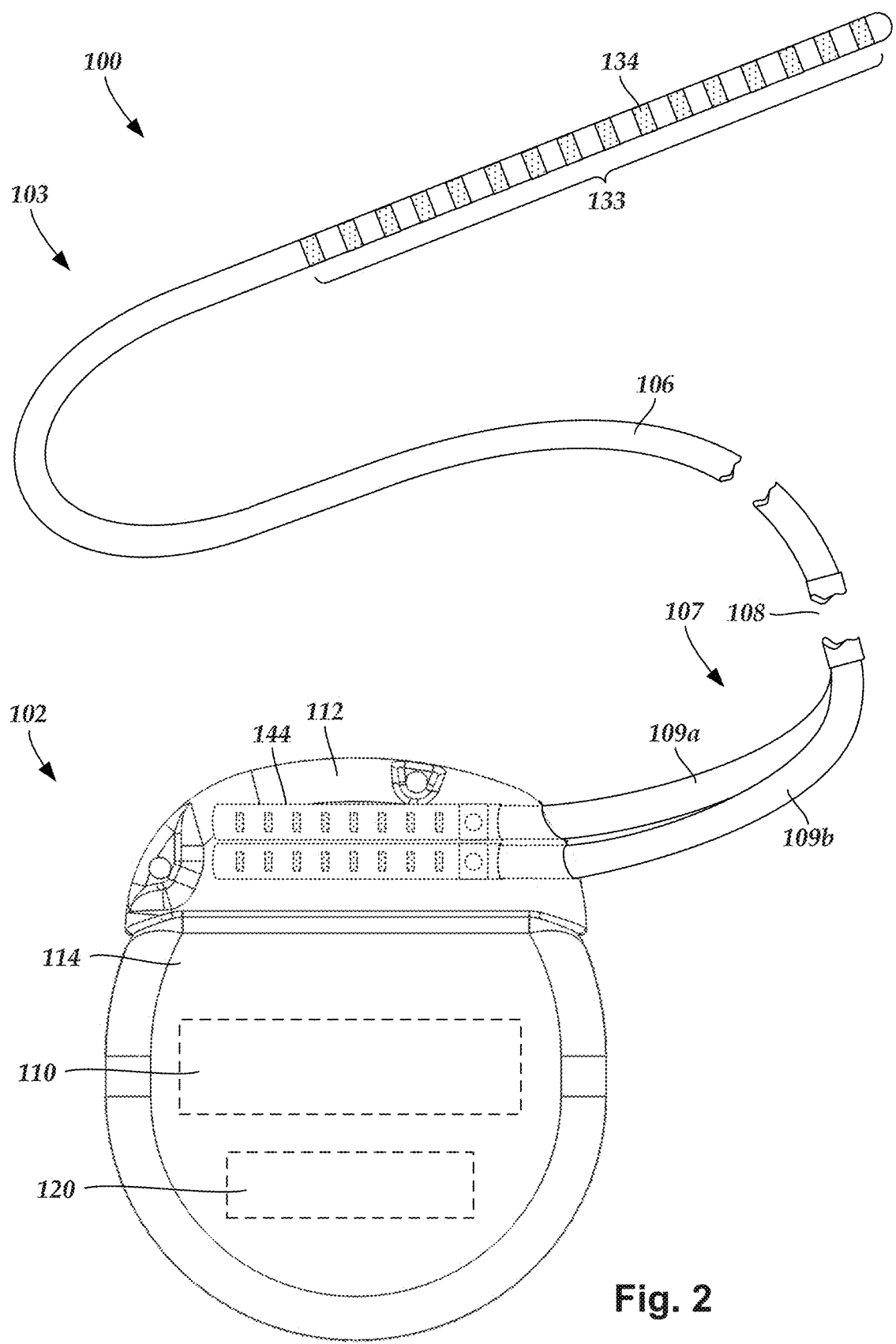
FIG. 2 is a schematic front view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the at least one lead body 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via at least one intermediate device (324 in FIG. 3B). For example, in at least some embodiments at least one lead extension 324 (see, for example, FIG. 3B) can be disposed between the lead 103 and the control module 102 to extend the distance between the lead 103 and the control module 102. Other intermediate devices may be used in addition to, or in lieu of, at least one lead extension including, for example, a splitter, an adaptor, or the like or combinations thereof. It will be understood that, in the case where the electrical stimulation system 100 includes multiple intermediate devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and at least one splitter tail 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system 100 or components of the electrical stimulation system 100, including the paddle body 104, the at least one of the lead bodies 106, and the control module 102, are typically implanted into the body of a patient. The electrical stimulation system 100 can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, at least one of the electrodes 134 are formed from at least one of: platinum, platinum iridium, palladium, palladium rhodium, or titanium.

Any suitable number of electrodes 134 can be disposed on the lead 103 including, for example, one, two, three, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes 134 of the paddle body 104 (or at least one lead body 106) are typically disposed in, or separated by, a non-conductive, biocompatible material such as, for example, silicone, polyurethane, polyetheretherketone ("PEEK"), epoxy, and the like or combinations thereof. The at least one lead body 106 and, if applicable, the paddle body 104 may be formed in the desired shape by any process including, for example, molding (including injection molding), casting, and the like. The non-conductive material typically extends from the distal ends of the at least one lead body 106 to the proximal end of each of the at least one lead body 106.

In the case of paddle leads, the non-conductive material typically extends from the paddle body 104 to the proximal end of each of the at least one lead body 106. Additionally, the non-conductive, biocompatible material of the paddle body 104 and the at least one lead body 106 may be the same or different. Moreover, the paddle body 104 and the at least one lead body 106 may be a unitary structure or can be formed as two separate structures that are permanently or detachably coupled together.

Figure 3A:
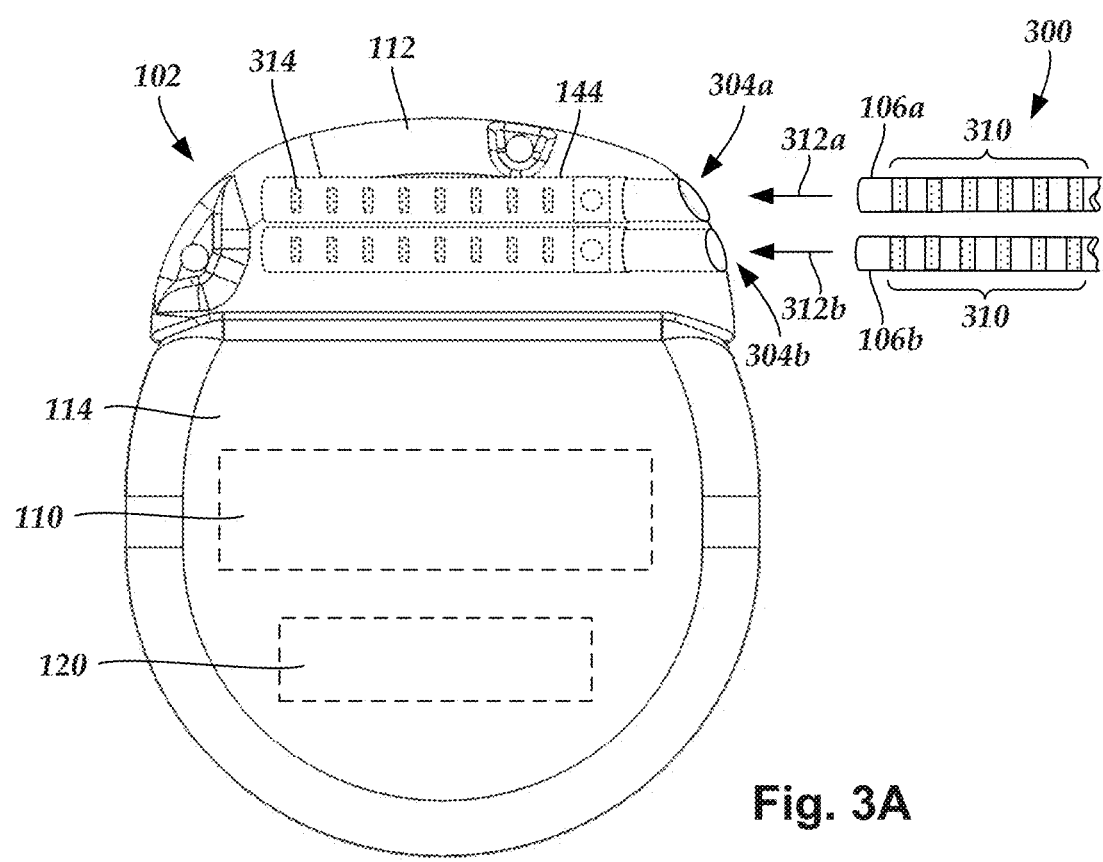
FIG. 3A is a schematic front view of one embodiment of the control module of FIG. 1 configured and arranged to electrically couple to a lead body, according to the invention.

Terminals (for example, 310 in FIG. 3A) are typically disposed along the proximal end of the at least one lead body 106 of the electrical stimulation system 100 (as well as any splitters, lead extensions, adaptors, or the like) for electrical connection to corresponding connector contacts (for example, 314 in FIG. 3A). The connector contacts are disposed in connectors (for example, 144 in FIGS. 1-3B; and 322 in FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, at least one electrode 134 are electrically coupled to each terminal. In at least some embodiments, each terminal is only connected to one electrode 134.

FIG. 3A is a schematic side view of one embodiment of a proximal end of at least one elongated device 300 configured and arranged for coupling to one embodiment of the control module connector 144. The at least one elongated device 300 may include, for example, at least one of the lead bodies 106 of FIG. 1, at least one intermediate device (for example, a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
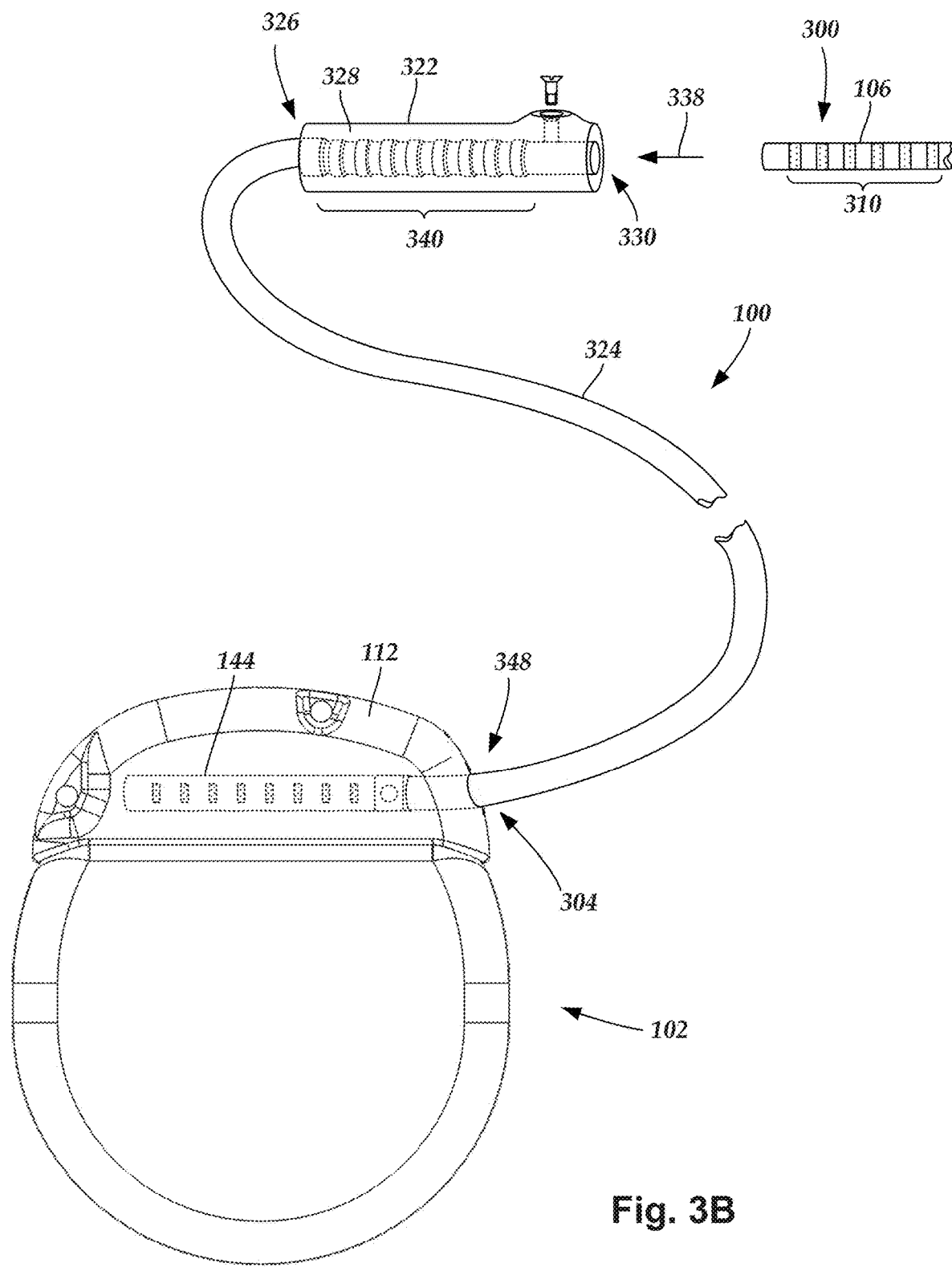
FIG. 3B is a schematic front view of one embodiment of a lead extension configured and arranged to electrically couple a lead body to a control module, according to the invention.

FIG. 3B is a schematic side view of another embodiment of the electrical stimulation system 100. The electrical stimulation system 100 includes a lead extension 324 that is configured and arranged to couple at least one elongated device 300 (for example, one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

The terms "proximal" and "distal" are used consistently with respect to all elements of the lead and system and are defined relative to the proximal end portion of the lead which attaches to the control module. The distal end portion of the lead has the electrodes disposed thereon.

Figure 4A:
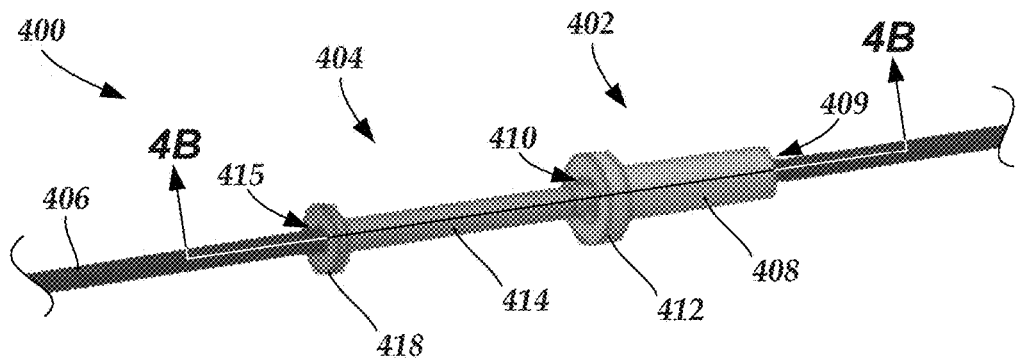
FIG. 4A is a schematic perspective view of a portion of one embodiment of an anchoring system, including a portion of a removable inner core inserted into a lead anchor, according to the invention.
Figure 4B:
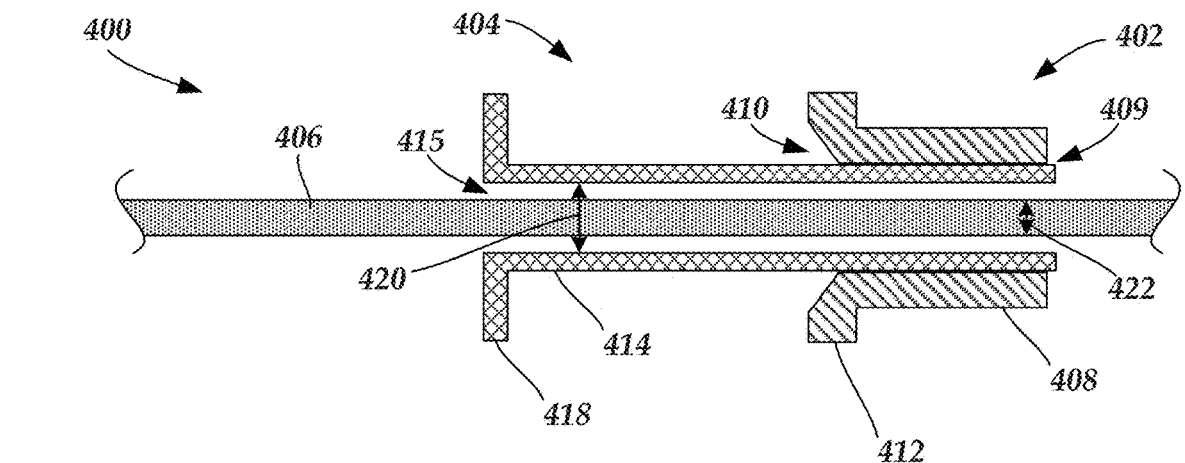
FIG. 4B is a schematic longitudinal cross-sectional view of one embodiment of the anchoring system of FIG. 4A taken at line 4B-4B, according to the invention.
Figure 4C:
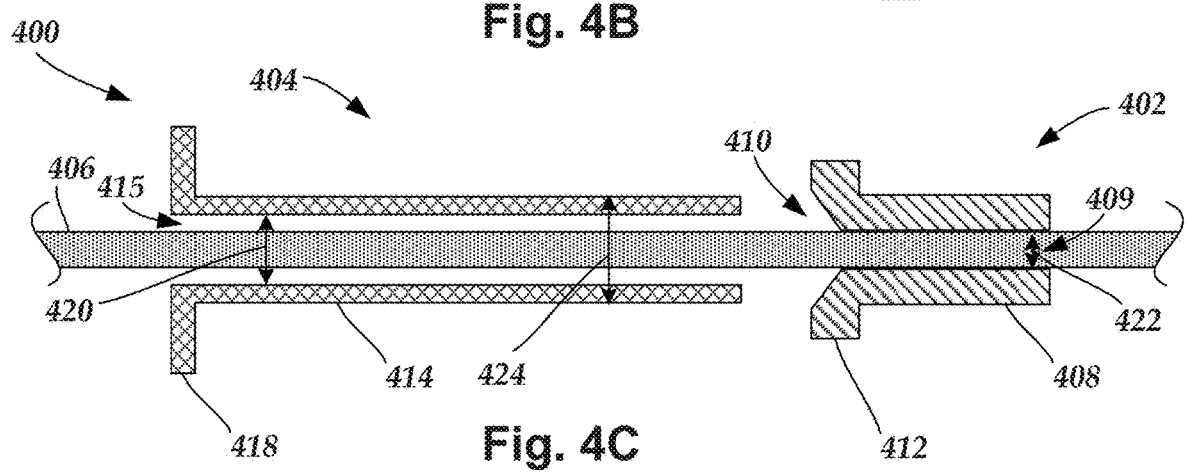
FIG. 4C is a schematic longitudinal cross-sectional view of one embodiment of the anchoring system of FIG. 4A with the removable inner core withdrawn from the lead anchor so that the lead anchor engages the lead body, according to the invention.

FIGS. 4A-4C illustrate one embodiment of a lead anchor 402 that can be attached to at least one lead or lead extension to facilitate anchoring the at least one lead or lead extension in patient tissue (for example, muscular tissue, connective tissue, organ tissue, bone, cartilage, nerve tissue, or the like). The lead anchor 402 engages or compresses the lead body 406 to anchor the lead to tissue but can be expanded for positioning or repositioning of the lead anchor on the lead or for removal of the lead anchor from the lead. In at least some embodiments, the lead anchor 402 is sutured to patient tissue to prevent or reduce lead migration (lateral, axial, or both) after implantation. The lead anchor 402 can be useful for leads for sacral nerve stimulation, spinal cord stimulation, or stimulation of other patient tissue.

FIG. 4A is a schematic perspective view of a portion of one embodiment of an anchoring system 400 that includes a lead anchor 402 and a removable inner core 404. FIG. 4B is a schematic cross-sectional view of the anchoring system 400 taken along line 4B-4B. FIGS. 4A and 4B illustrate the lead anchor 402 loaded on the removable inner core 404. This is an expanded configuration of the lead anchor 402. In the expanded configuration, the inner core 404 expands the inner diameter of the lead anchor 402 so that the lead anchor can be positioned or repositioned along the lead body 406 or removed from the lead body 406.

The lead anchor 402 has an anchor body 408 that forms a lead lumen 409. The lead lumen 409 can have any suitable cross-sectional shape that corresponds to the shape of the lead body 406. In the illustrated embodiment, the cross-sectional shape of the lead lumen is circular, but other embodiments may have a rectangular, elliptical, square, triangular, or any other suitable shape. The lead lumen 409 has an inner diameter that, when not expanded by the inner core, is equal to or slightly less than the diameter 422 of the lead body 406. In at least some embodiments, this inner diameter is in the range of 0.1 to 2 mm or more. In at least some embodiments, the lead lumen 409 has a slit along an entirety of the length of the anchor body 408. In at least some embodiments, when the lead anchor 402 is sutured to the patient, the sutures compress the slit.

In the illustrated embodiment, at least one end of the anchor body 408 (for example, the proximal end, the distal end, or both) includes a countersink 410. The countersink may facilitate loading the lead anchor 402 onto the removable inner core 404.

In at least some embodiments, the lead anchor 402 has at least one flange 412 that radially extends from the anchor body 408 (for example, at least one of the proximal end portion, the middle portion, or the distal end portion, or any combination thereof). The flange 412 may increase surface area for applying axial force to the lead anchor 402 during removal or loading of the inner core 404. Additionally or alternatively, the anchor body 408 may have a radial thickness 434 that provides sufficient surface area to apply sufficient axial force to load the lead anchor 402 onto the removable inner core 404, unload the lead anchor 402 from the removable inner core 404, or both.

The lead anchor 402 may be made from any resilient biocompatible material including polymeric materials, such as, but not limited to, silicone, polyurethane, polyetheretherketone, or other suitable materials. In at least some embodiments, the lead anchor 402 has a length of 0.5, 1, 2, 3, 4, or 5 cm or more. In at least some embodiments, the anchor body 408 has a substantially cylindrical shape, but any other suitable shapes can be used. The lead anchor 402 may be made via any suitable molding (for example, injection molding), casting, or other process. The lead anchor 402 may be made as a unitary or non-unitary structure.

The removable inner core 404 has a core body 414 that forms an inner lumen 415. The inner lumen 415 of the illustrated embodiment has a circular cross-section, but any other suitable cross-section corresponding to a shape of the lead body can be used.

The inner lumen 415 may have an inner diameter 420 that is greater than the outer diameter 422 of the lead body 406 (for example, at least 0.5, 1, 1.5, 2, 3, 4, 5 mm or more). Optionally, the removable inner core 404 may include a narrowing portion at the end to be inserted into the lead anchor 402 to facilitate insertion. The outer surface of the narrowing portion may have a slope of at least 5, 15, 30, 45, 60, or 75 degrees.

In at least some embodiments, the removable inner core 404 has at least one flange 418 that radially extends from the outer surface of the core body 414 (for example, at the proximal end portion, the middle portion, or both). In at least some embodiments, the removable inner core 404 has a slit along an entirety of the length of the removable inner core 404 to facilitate loading the removable inner core 404 onto the lead body 406. In at least some embodiments, the width of the slit is, at least when the lead anchor 402 is unloaded from the inner core 404, greater than the diameter of the lead body 406. Otherwise, the inner core 404 is loaded onto the lead body 406 by sliding from one end of the lead body 406.

The removable inner core 404 may be made from any rigid material, such as metal, alloy, polymer, or other suitable mineral or any combination thereof. The removable inner core 404 has a length that is at least as long as the lead anchor 402 (for example, at least 1, 2, 3, 4, 5 cm or more). In the illustrated embodiment, the core body 414 has a substantially cylindrical shape, but other suitable shapes can be used. The removable inner core 404 may be made as a unitary or non-unitary structure, with or without adhesive, welding, soldering, brazing, mechanical joints, or the like.

Loading the lead anchor 402 onto the core body 414 of the removable inner core 404 expands the diameter of the lead lumen 409 of the lead anchor 402 to be greater than the diameter 422 of the lead body 406. In the expanded configuration, the lead anchor 402 can be positioned or repositioned along the lead body 406 or removed from the lead body 406 with the removable inner core 404.

FIG. 4C is a schematic longitudinal cross-sectional view of the anchoring system 400 with the lead anchor 402 unloaded from the removable inner core 404 and anchored to the lead body 406. When the lead anchor 402 is attached to the lead body 406 after removal of the removable inner core 404, the lead lumen 409 of the lead anchor 402 contracts to form an engagement or compression or friction fit with the lead body 406. This is an engagement configuration of the lead anchor 402. In the engagement configuration, the location of the lead anchor 402 relative to the lead body 406 is fixed so that the lead anchor 402 will not move axially relative to the lead body 406 in order to anchor the lead body 406 to tissue.

In at least some embodiments, the surface of the lead lumen 409 of the anchor body 408 has a ribbed, toothed, textured, threaded, micro-patterned, or otherwise roughened inner surface or any combination thereof to facilitate or enhance engagement with the lead body 406.

The lead anchor 402 may be sutured to the patient's tissue. In at least some embodiments, the sutures can wrap around the lead anchor 402 and may further constrict the lead anchor 402 where the sutures wrap around the lead anchor 402 to secure the lead anchor 402 to the tissue.

Figure 4D:
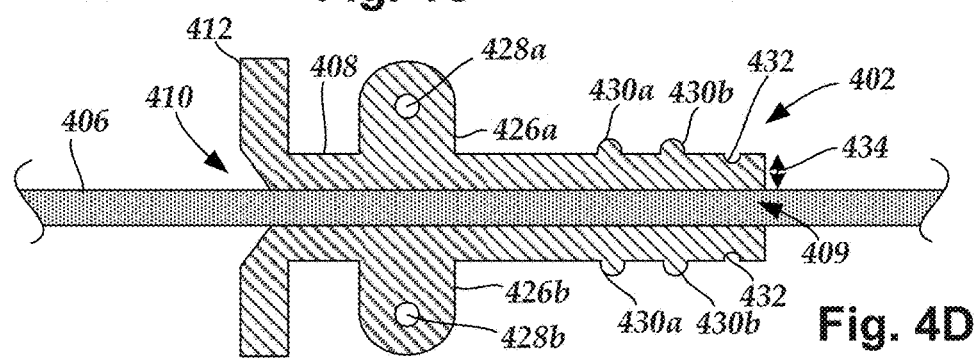
FIG. 4D is a schematic longitudinal cross-sectional view of another embodiment of a lead anchor disposed on a lead body, according to the invention.

In at least some embodiments, the lead anchor 402 includes one or more additional features that facilitate securing the lead anchor 402 to the tissue, as illustrated in FIG. 4D. One example is suture tabs 426a, 426b that radially extend from the anchor body 408. The suture tabs 426a, 426b may include suture holes 428a, 428b. The lead anchor 402 may have at least one, two, three, or four suture tabs. The suture tabs may be uniformly or nonuniformly longitudinally or circumferentially offset from each other (for example, spaced apart from each other by 60°, 90°, 120°, or 180° around the circumference of the anchor body 408, or any combination thereof).

Additionally or alternatively, the lead anchor 402 may have at least one, two, three, or four suture regions. Each suture region may be defined between ridges 430a, 430b on each side of the suture trough. Yet another feature for securing the lead anchor to tissue is a groove 432. Each suture region, ridge, or groove may form a complete or partial ring or helix around the anchor body 408. A lead anchor can include one or more suture tabs, one or more suture regions with ridges, one or more grooves, or any combination thereof.

In at least some embodiments, the lead anchor 402 has at least one, two, three, or four strain-relief grooves (not shown) that extend circumferentially around at least one portion of the anchor body 408 to reduce strain exerted on the lead body 406 by increasing flexibility of the lead anchor.

In at least some embodiments, the lead anchor 402 can be loaded onto or unloaded from the removable inner core 404 by a user applying sufficient axial force to the lead anchor 402, the removable inner core 404, or both, to push the lead anchor onto the inner core or to push the inner core into the lead anchor. The user may apply the axial force by hand or with a tool, such as forceps, tweezers, a specialized tool, or the like. In at least some embodiments, the removable inner core 404 is a non-removable part of the tool.

FIGS. 5A-5E illustrate one embodiment of a tool 500 that can be used to remove the inner core 404 from the lead anchor 402 in order to anchor the lead anchor 402 on the lead and, in at least in some embodiments, may be used to reinsert the removable inner core 404 into the lead anchor 402 for repositioning or removing the lead anchor 402 from the lead. In at least some embodiments, the tool 500 includes a rail component 502 and a slide component 504 that travels along the rail component 502. In the illustrated embodiment, the rail component 502 includes two rails 506a, 506b, although in other embodiments the rail component 502 can have one, three, or more rails. In at least some embodiments, the rails 506a, 506b have lengths that permit the slide component 504 to travel a distance that is at least as long as the removable inner core 404.

Figure 5A:
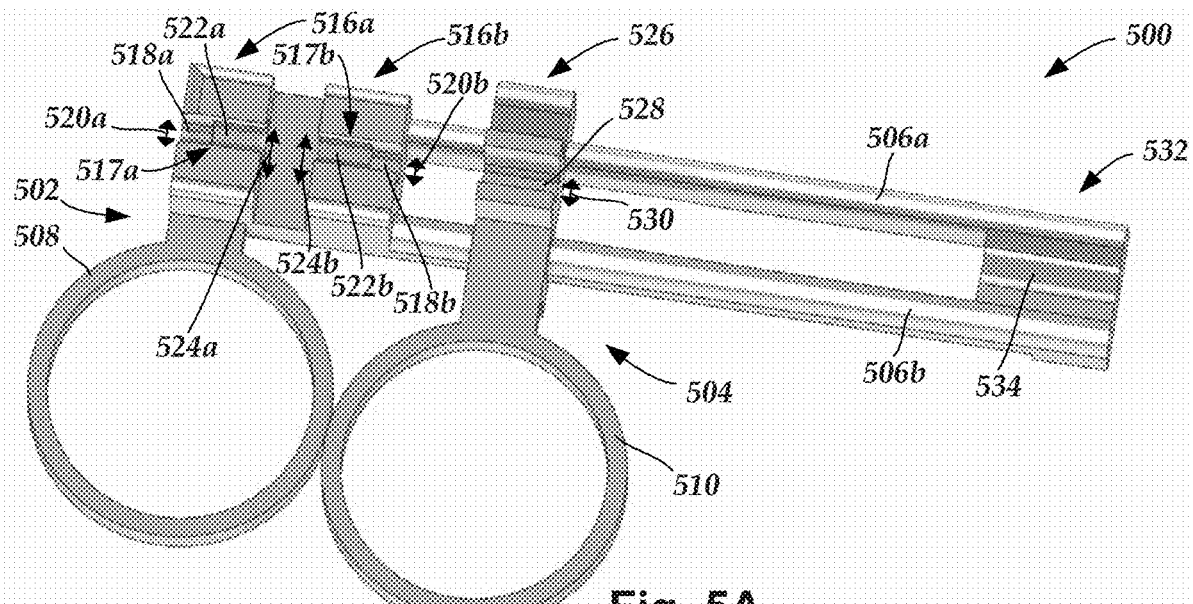
FIG. 5A is a schematic perspective view of one embodiment of a tool, according to the invention.
Figure 5B:
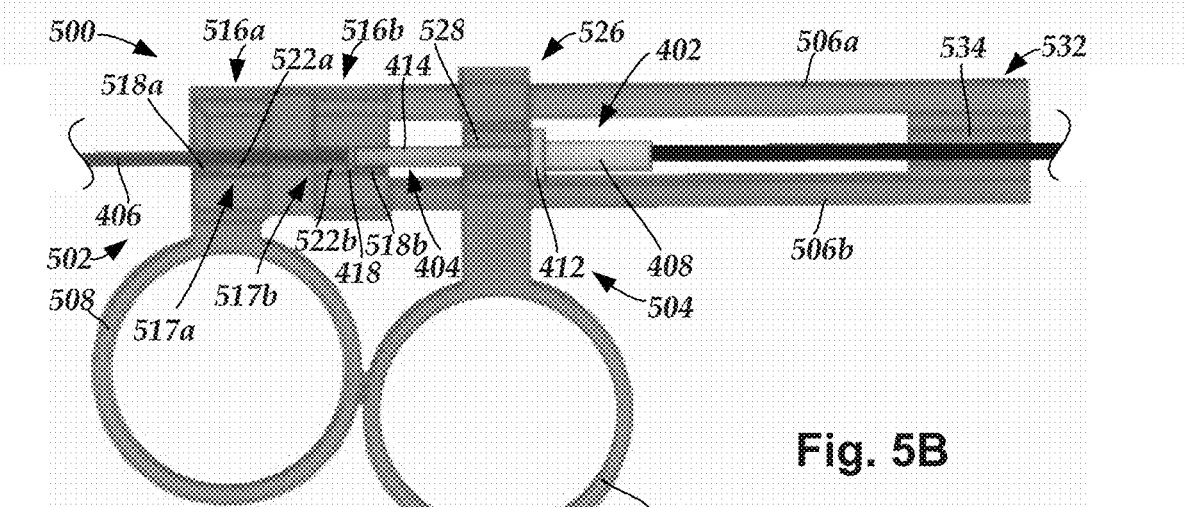
FIG. 5B is a schematic perspective view of one embodiment of the tool of FIG. 5A with the tool positioned to withdraw the removable inner core from the lead anchor, according to the invention.
Figure 5C:
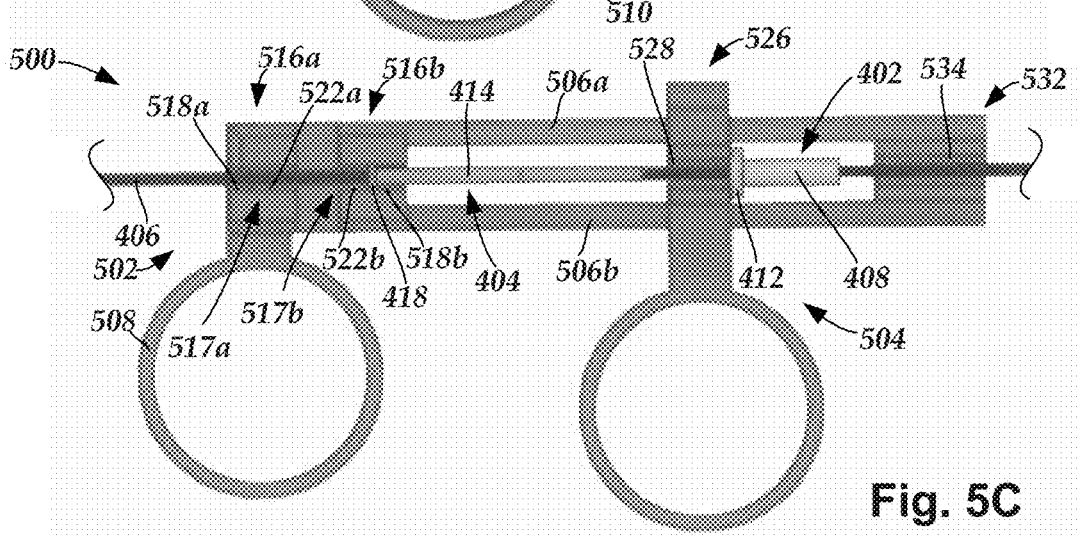
FIG. 5C is a schematic perspective view of one embodiment of the tool of FIG. 5A with removable inner core withdrawn from the lead anchor, according to the invention.
Figure 5D:
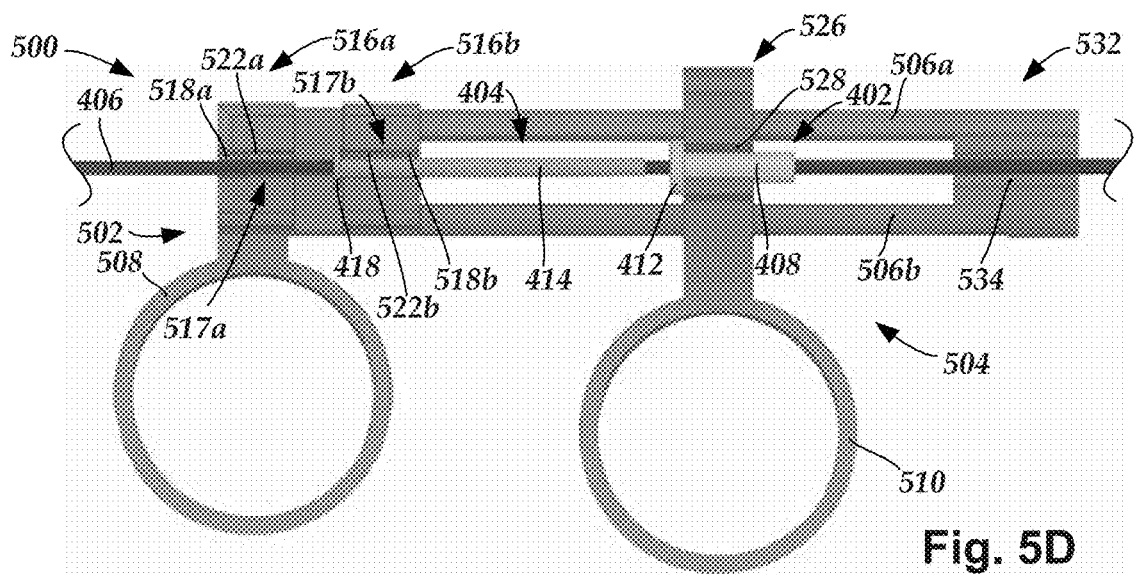
FIG. 5D is a schematic perspective view of one embodiment of the tool of FIG. 5A with the tool positioned to reinsert the removable inner core into the lead anchor, according to the invention.
Figure 5E:
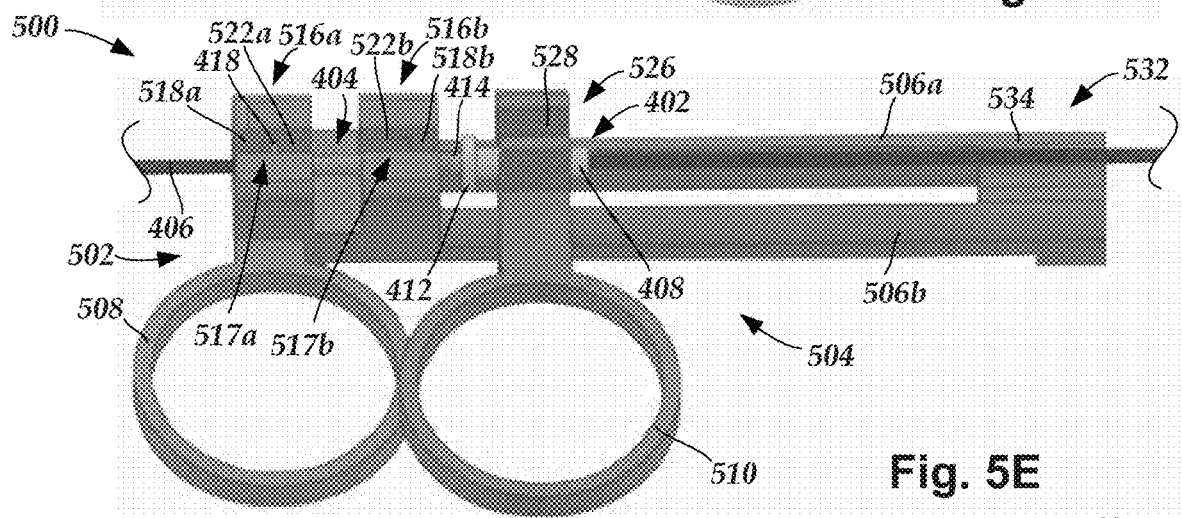
FIG. 5E is a schematic perspective view of one embodiment of the tool of FIG. 5A with the removable inner core reinserted into the lead anchor, according to the invention.

In at least some embodiments, the rail component 502 and the slide component 504 each have at least one operation member 508, 510 by which the user operates the tool. In the illustrated embodiment, the operation members 508, 510 are rings (although shapes other than circular may also be used) that are each sized to receive an adult human finger or a tool, such as forceps. In other embodiments, at least one of the operation members 508, 510 may be a finger tang, slide, or other graspable or user-operable member, or the like. In the illustrated embodiment, the operation members 508, 510 are vertically offset from each other to permit sliding the slide component 504 to a location where the operation members 508, 510 approach or overlap each other (FIG. 5E).

In the illustrated embodiment, the proximal end portion of the rail component 502 has two receiving members 516a, 516b that are arranged for receiving the portion of the inner core 404 containing the flange 418. In other embodiments, the rail component 502 has one receiving member. In at least some embodiments, the receiving members 516a, 516b have channels 517a, 517b with narrow portions 518a, 518b that have narrow channel diameters 520a, 520b that are less than the diameter of the flange 418 of the removable inner core 404 yet greater than the outer diameter 424 of the core body 414. In at least some embodiments, the channels 517a, 517b of the receiving members 516a, 516b have wide portions 522a, 522b that have wide channel diameters 524a, 524b that are sized to receive the flange 418 of the removable core 404. In other embodiments, the narrow channel diameters 520a, 520b are less than the outer diameter of the anchor body 408 or the flange 412 of the lead anchor 402 in the engagement configuration yet greater than the diameter 422 of the lead body 406. In at least some embodiments, the channel 517b of the receiving member 516b is used during removal of the inner core 404 from the lead anchor 402 (see, FIGS. 5B and 5C), and the channel 517a of the receiving member 516a is used to reinsert the removable inner core 404 into the lead anchor 402 (see, FIGS. 5D and 5E).

In the illustrated embodiment, the slide component 504 has one receiving member 526, yet in other embodiments the slide component 504 has two receiving members. In at least some embodiments, the receiving member 526 has a channel 528 that has a diameter 530 that is less than the outer diameter of the flange 412 of the lead anchor 402 and, optionally, less than the diameter of the anchor body 408 of the lead anchor 402 in the engagement configuration yet greater than the diameter 422 of the lead body 406. In other embodiments, the diameter 530 is less than the diameter of the flange 418 of the inner core 404 yet greater than the outer diameter 424 of the core body 414. In at least some embodiments, each of the receiving members 516a, 516b, and 526 is dimensioned to receive and stop both the lead anchor 402 and the inner core 404.

In the illustrated embodiment, the distal end portion of the rail component 502 has a supporting member 532 that bridges the rails 506a, 506b. In at least some embodiments, the supporting member 532 has a channel 534 that is dimensioned to receive and support the lead body 406.

The lead anchor 402, with the removable inner core 404 inserted, is slid or otherwise placed on the lead and moved to the desired anchoring position along the lead. When the lead anchor 402 is in the desired position, the inner core 404 can now be withdrawn from the lead anchor 402. The lead body 406, lead anchor 402, and inner core 404 are loaded into the channels 517a, 517b, 528, 534 of the tool 500 as illustrated in FIG. 5B. The lead anchor 402 is positioned with the flange 412 of the lead anchor 402 adjacent the slide component 504 and the flange 418 of the inner core 404 is positioned proximal of the narrow portion 518b of the channel 517b. The user then operates the tool 500 to remove the inner core 404 from the lead anchor 402 by separating the slide component 504 from the rail component 502, as illustrated in FIG. 5C. This pushes the lead anchor 402 distally while holding the inner core 404 stationary (or pulls the inner core 404 proximally while holding the lead anchor 402 stationary) so that the inner core 404 is removed from the lead lumen 409 of the anchor body 408. The anchor body 408 then engages or compresses the lead body 406 to anchor the lead anchor 402 to the lead body 406.

After removing the inner core 404 from the lead anchor 402, the user can remove the lead body 406 from the tool 500. In at least some embodiments, the user can remove the inner core 404 from the lead body 406 by sliding the inner core 404 proximally along the lead body 406 and off the proximal tip of the lead. In other embodiments, the inner core 404 has a slit (not shown) along the longitudinal length of the core body 414 that enables the user to remove the inner core 404 from the lead body 406 by removing the lead body 406 from the inner lumen 415 of the inner core 404 through the slit.

When the lead anchor 402 is to be removed from or repositioned on the lead body 406, the inner core 404 can be slid or otherwise placed on the lead and moved proximal the lead anchor 402 on the lead body 406. As shown in FIG. 5D, with the inner core adjacent the lead anchor 402 on the lead body, the lead body 406 can be placed in the channels 517a, 517b, 528, 534 with the flange 418 of the inner core 404 distal to the narrow portion 518a and the flange 412 proximal to the channel 528. The user then operates the tool 500 to insert the inner core 404 into the lead lumen 409 of the lead anchor 402 by sliding the slide component 504 toward the rail component 502 (or sliding the rail component 502 toward the slide component 504). This pushes the inner core 404 distally (using receiving member 516a as a stop) while holding the inner core 404 stationary (or pulls the inner core 404 proximally while holding the lead anchor 402 stationary, again using receiving member 516a as a stop) so that the inner core is inserted into the lead lumen 409 of the anchor body 408. The lead anchor 402, with the removable inner core 404 inserted, can be slid or otherwise removed from the lead or repositioned to a desired anchoring position along the lead. When the lead anchor 402 is in the desired position, the inner core 404 can now be withdrawn from the lead anchor 402 as explained above.

In at least some embodiments, the removable inner core 404 is a non-removable part of the rail component 502 or the slide component 504. In at least some embodiments, the tool 500 is made from any rigid material, such as metal, alloy, polymer, or other suitable mineral or any combination thereof.

Figure 6:
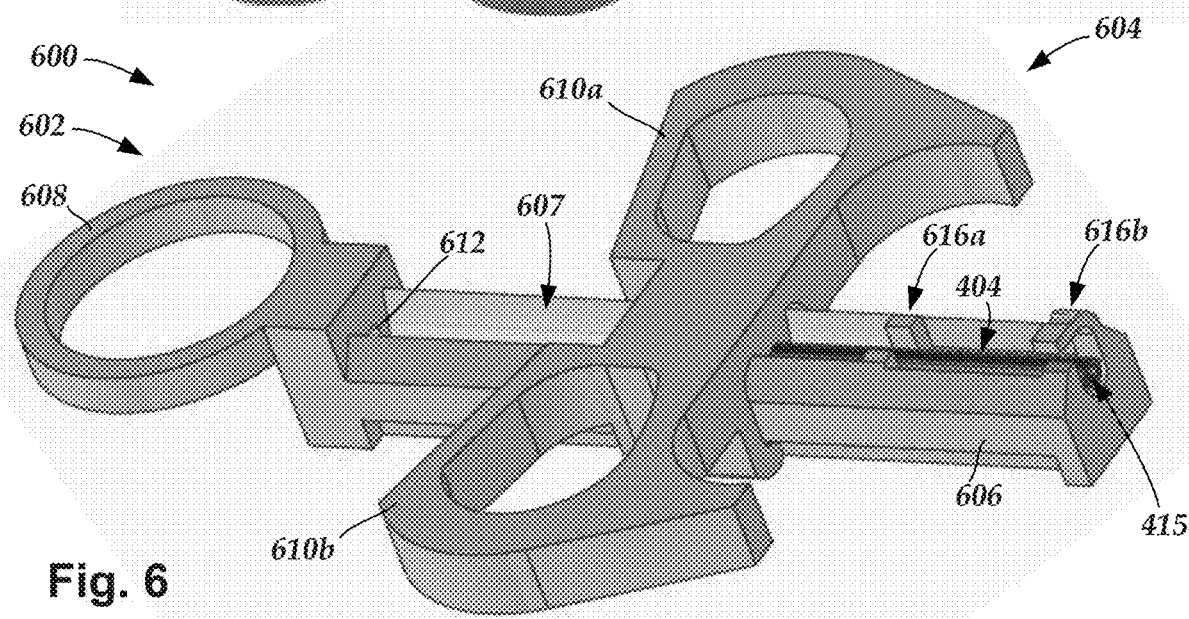
FIG. 6 is a schematic perspective view of another embodiment of a tool, according to the invention.

FIG. 6 illustrates another embodiment of a tool 600 that can be used to remove the lead anchor 402 from the removable inner core 404 in order to anchor the lead anchor 402 on the lead and, in at least some embodiments, may be used to reinsert the inner core 404 into the lead anchor 402 for repositioning or removing the lead anchor 402 from the lead. In at least some embodiments, the tool 600 includes a rail component 602 and a slide component 604 that travels along the rail component 602. In the illustrated embodiment, the rail component 602 includes a rail 606, yet in other embodiments the rail component 602 has two, three, or more rails. In at least some embodiments, the rail 606 has a length that permits the slide component 604 to travel a distance that is at least as long as the removable inner core 404.

In at least some embodiments, the inner core 404 is part of the slide component 604. In at least some embodiments, the inner core 404 is an integral part of the slide component 604. In other embodiments, the inner core 404 is attached to the slide component 604 via any suitable method, such as welding, adhesive, threads on the outer surface of proximal end portion of the inner core 404 that match threads on the inner surface of the slide component 604, or the like. In yet other embodiments, the inner lumen 415 of the inner core 404 extends through the slide component 604. In at least some embodiments, the tool 600 is made from any rigid material, such as metal, alloy, polymer, or other suitable mineral or any combination thereof. In at least some embodiments, the inner core 404 is made of the same or different material as the tool 600.

In at least some embodiments, the rail component 602 has a proximal lumen 612 through the rail component 602 that has a diameter that is greater than the diameter 422 of the lead body 406. The user can insert the proximal end portion of the lead into the inner lumen 415 of the inner core 404 and through the proximal lumen 612. The rail 606 defines a channel 607 that can support the lead body 406 when the lead is inserted through the inner lumen 415 and the proximal lumen 612. The channel 607 has a diameter that is at least as great as the largest diameter of the lead anchor 402.

The rail component 602 and the slide component 604 each have at least one operation member 608, 610a, 610b by which the user operates the tool 602 while the lead body 406 lies in the channel 607. In the illustrated embodiment, the distal end portion of the channel 607 has two narrow portions 616a, 616b, yet in other embodiments the channel 607 has one narrow portion, such as the narrow portion 616a. The narrow portions 616a, 616b have narrow channel diameters that are less than the diameter of the flange 412 of the lead anchor 402 or the anchor body 408 yet greater than the outer diameter 424 of the core body 414.

To insert the inner core 404 into the lead anchor 402, the slide component 604 is positioned at or near the proximal end of the rail 606 and the lead anchor 402 is placed in the channel 607 with the flange 412 of the lead anchor 402 between the narrow portions 616a, 616b. The operation members 610a, 610b can be moved away from the operation member 608, inserting the inner core 404 into the lead lumen 409 of the lead anchor 402. When the inner core 404 is inserted into the lead lumen 409 of the lead anchor 402, the proximal end portion of the lead is inserted through the inner lumen 415 of the inner core and the proximal lumen 612 of the rail component 602. The tool 600 is slid along the lead body 406 to the desired anchoring position along the lead. When the lead anchor 402 is in the desired position, the operation members 610a, 610b can be moved toward the operation member 608. This pulls the inner core 404 proximally while holding the lead anchor 402 stationary so that the inner core 404 is removed from the lead lumen 409 of the lead anchor 402. The anchor body 408 then compresses against the lead body 406 to anchor the lead anchor 402 to the lead body 406. In at least some embodiments, the user can slide the tool 600 along the lead body 406 and off the proximal tip of the lead.

When the lead anchor 402 should be removed from or repositioned on the lead body 406, the tool 600 can be configured to load the lead anchor 402 from the lead body 406 onto the inner core 404. With the slide component 604 positioned at the proximal end of the rail 606, the proximal end portion of the lead is inserted through the inner lumen 415 of the inner core and the proximal lumen 612 of the rail component 602. The tool 600 can be slid along the lead body 406. Once the flange 412 of the lead anchor 402 aligns with the portion of the channel 607 between the narrow portions 616a, 616b, the lead body 406 and lead anchor 402 can be dropped into the portion of the channel 607 between the narrow portions 616a, 616b. When the flange 412 of the lead anchor 402 is positioned between the narrow portions 616a, 616b, the operation members 610a, 610b can be pulled away from the operation member 608 to insert the inner core 404 into the lead lumen 409 of the lead anchor 402. The tool 600 with the lead anchor 402 can be slidably removed from the lead body 406. Alternatively, the tool 600 with the lead anchor 402 can be slid to the desired anchoring position along the lead. When the lead anchor 402 is in the desired position, the operation members 610a, 610b can be pulled toward the operation member 608 to remove the inner core 404 from the lead lumen 409 of the lead anchor 402 as explained above.

Figure 7:
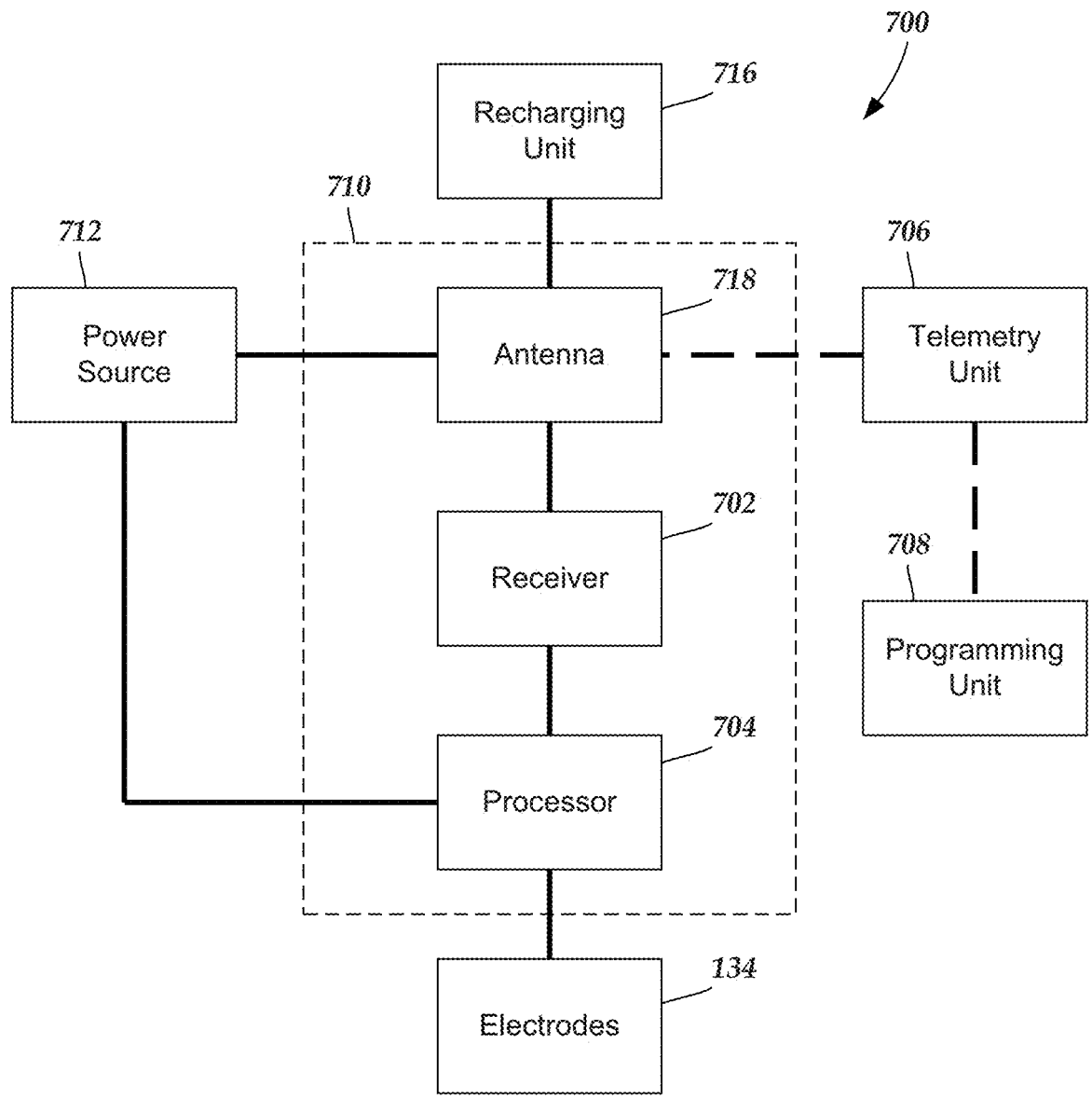
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on at least one circuit board or similar carrier within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, or in addition, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control at least one of the timing, frequency, strength, duration, and waveform of the pulses. In addition, the processor 704 can select which electrodes can be used to provide stimulation, if desired. In at least some embodiments, the processor 704 selects which electrode(s) are cathodes and which electrode(s) are anodes. In at least some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (for example, RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying at least one of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification provides a description of the invention and the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A stimulation lead anchoring system, comprising:
   a lead anchor comprising an anchor body, wherein the anchor body comprises a distal end portion, a proximal end portion, a longitudinal length, and a lead lumen that extends longitudinally along the anchor body and is configured and arranged to receive a portion of an electrical stimulation lead; and
   a removable inner core comprising a core body, wherein the core body comprises a distal end portion, a proximal end portion, a longitudinal length, and an inner lumen that extends longitudinally along the core body,
   wherein the lead anchor and removable inner core are configured and arranged to expand the anchor body into an expanded configuration when a portion of the core body is inserted into the lead lumen of the anchor body to facilitate receiving the portion of the electrical stimulation lead into the lead lumen of the lead anchor and the inner lumen of the removable inner core and slidably positioning the lead anchor at a selected position along the electrical stimulation lead, wherein the anchor body is configured and arranged to engage the portion of the electrical stimulation lead in the lead lumen upon withdrawal of the core body of the removable inner core from the lead lumen of the anchor body.

2. The stimulation lead anchoring system of claim 1, wherein the longitudinal length of the core body is at least as long as the longitudinal length of the anchor body.

3. The stimulation lead anchoring system of claim 1, wherein the core body further comprises a slit that extends along the longitudinal length of the core body.

4. The stimulation lead anchoring system of claim 1, wherein the anchor body is configured and arranged to compress the portion of the electrical stimulation lead in the lead lumen upon withdrawal of the core body of the removable inner core from the lead lumen of the anchor body.

5. The stimulation lead anchoring system of claim 1, wherein the lead anchor further comprises at least one suture tab that radially extends from the anchor body.

6. The stimulation lead anchoring system of claim 1, wherein the lead anchor further comprises at least two ridges that radially extend from the anchor body and that define at least one suture region between the at least two ridges.

7. The stimulation lead anchoring system of claim 1, wherein the lead anchor further comprises at least one suture trough or groove in the anchor body.

8. The stimulation lead anchoring system of claim 1, wherein the lead anchor further comprises a flange that radially extends from either the proximal end portion or distal end portion of the anchor body.

9. The stimulation lead anchoring system of claim 1, wherein the removable inner core further comprises a flange that radially extends from the proximal end portion of the core body.

10. The stimulation lead anchoring system of claim 9, further comprising a tool comprising:
    a rail component, wherein the rail component comprises at least one channel, wherein at least one portion of the at least one channel of the rail component has a diameter that is at least as large as an outer diameter of the core body and is smaller than an outer diameter of the flange of the removable inner core; and
    a slide component configured and arranged to slide along the rail component, wherein the slide component comprises at least one channel, wherein at least one portion of the at least one channel of the slide component has a diameter that is at least as large as the outer diameter of the core body and is smaller than an outer diameter of at least one portion of the lead anchor.

11. The stimulation lead anchoring system of claim 9, further comprising a tool comprising:
    a rail component, wherein the rail component comprises at least one channel, wherein at least one portion of the at least one channel of the rail component has a diameter that is at least as large as an outer diameter of the core body and is smaller than an outer diameter of at least one portion of the lead anchor; and a slide component configured and arranged to slide along the rail component, wherein the slide component comprises at least one channel, wherein at least one portion of the at least one channel of the slide component has a diameter that is at least as large as the outer diameter of the core body and is smaller than an outer diameter of the flange of the removable inner core.

12. The stimulation lead anchoring system of claim 1, further comprising a tool comprising:

a rail component, wherein the rail component comprises at least one channel, wherein at least one portion of the at least one channel of the rail component has a diameter that is at least as large as an outer diameter of the core body and is smaller than an outer diameter of at least one portion of the lead anchor; and a slide component configured and arranged to slide along the rail component, wherein the removable inner core is integral to, or non-removably attached to, the slide component.

13. The stimulation lead anchoring system of claim 1, further comprising the electrical stimulation lead.

14. A method of anchoring an electrical stimulation lead with the stimulation lead anchoring system of claim 1, the method comprising:

inserting the portion of the electrical stimulation lead in the lead lumen of the anchor body of the lead anchor and the inner lumen of the core body of the removable inner core while a portion of the core body of the removable inner core is disposed within the lead lumen of the anchor body of the lead anchor;

withdrawing the core body of the removable inner core from the lead lumen of the anchor body of the lead anchor so that the lead anchor engages the electrical stimulation lead; and removing the removable inner core from the electrical stimulation lead.

15. The method of claim 14, wherein the lead anchor further comprises a flange that radially extends from the proximal or distal end portion of the anchor body, wherein withdrawing the core body of the removable inner core from the lead lumen of the anchor body of the lead anchor comprises applying a force against the flange of the lead anchor.

16. The method of claim 14, wherein the removable inner core further comprises a flange that radially extends from the proximal end portion of the core body, wherein withdrawing the core body of the removable inner core from the lead lumen of the anchor body of the lead anchor comprises applying a force against the flange of the removable inner core.

17. The method of claim 14, further comprising:

inserting another portion of the core body into the lead lumen of the anchor body;

repositioning the lead anchor and removable inner core on the electrical stimulation lead to another position on the electrical stimulation lead while the other portion of the core body is disposed within the lead lumen of the anchor body; and withdrawing the core body of the removable inner core from the lead lumen of the anchor body of the lead anchor so that the lead anchor engages the electrical stimulation lead at the other position on the electrical stimulation lead.

18. The method of claim 14, further comprising:

inserting another portion of the core body into the lead lumen of the anchor body; and removing the lead anchor and removable inner core from the electrical stimulation lead while the other portion of the core body is disposed within the lead lumen of the anchor body.

19. A method of employing the stimulation lead anchoring system of claim 1, the method comprising:

inserting a portion of the core body into the lead lumen of the anchor body; and removing the lead anchor and removable inner core from, or repositioning the lead anchor and removable inner core on, the electrical stimulation lead while the portion of the core body is disposed within the lead lumen of the anchor body.

20. The method of claim 19, wherein the lead anchor further comprises a flange that radially extends from the proximal or distal end portion of the anchor body, wherein inserting the core body into the lead lumen of the anchor body comprises applying a force against the flange of the lead anchor.

* * * * *